United States Patent [19] [11] 4,005,089
Mago nee Karacsony et al. [45] Jan. 25, 1977

[54] COMPOUNDS WITH ERGOLINE SKELETON

[75] Inventors: Erzsébet Magó nee Karácsony; József Borsi; Endre Csányi; Katalin Pik; Lajos Wolf, all of Budapest, Hungary

[73] Assignee: Richter Gedeon Vegyeszeti Gyar Rt., Budapest, Hungary

[22] Filed: May 22, 1975

[21] Appl. No.: 579,979

[30] Foreign Application Priority Data
May 28, 1974 Hungary .............................. GO1272

[52] U.S. Cl. .............................. 260/285.5; 424/261
[51] Int. Cl.$^2$ ........................................ C07D 457/06
[58] Field of Search .................. 260/285.5; 424/261

[56] References Cited
UNITED STATES PATENTS

| 2,533,699 | 12/1950 | Stoll et al. | 260/285.5 |
|---|---|---|---|
| 2,673,850 | 3/1954 | Stoll et al. | 260/285.5 |
| 2,946,796 | 7/1960 | Rudmer | 260/285.5 |
| 3,901,893 | 8/1975 | Karácsony et al. | 260/285.5 |

FOREIGN PATENTS OR APPLICATIONS

| 1,345,546 | 1/1974 | United Kingdom | 260/285.5 |
|---|---|---|---|

Primary Examiner—Donald G. Daus
Assistant Examiner—Mary C. Vaughn
Attorney, Agent, or Firm—Young & Thompson

[57] ABSTRACT

New compounds of the general formula (I)

$$\text{(I)}$$

wherein
R stands for hydrogen or methyl group,
$\widehat{xy}$ stands for a group of the formula $$-CH=C- \quad \text{or} \quad -CH_2-CH-,$$

and
$R_1$ stands for a group of the formula (III), (IV) or (V)

$$-\underset{O}{\overset{\|}{C}}-NH-CH_2-CH-CH_2-O-CH_2-CH=CH_2 \quad \text{(III)}$$
$$\underset{}{\phantom{xxxxxxxxxx}}O-\underset{O}{\overset{\|}{C}}-(CH_2)_n-CH_3$$

$$-\underset{O}{\overset{\|}{C}}-NH-CH-(CH_2)_3-NH-\underset{NH}{\overset{\|}{C}}-NH-NO_2 \quad \text{(IV)}$$
$$\phantom{xxxxxx}CH_2-O-\underset{O}{\overset{\|}{C}}-(CH_2)_n-CH_3$$

$$-CH_2-NH-\underset{O}{\overset{\|}{C}}-CH-NH-\overset{O}{\overset{\|}{C}}-O-CH_2-C_6H_5 \quad \text{(V)}$$
$$\phantom{xxxxxxxxx}CH_2-O-\underset{O}{\overset{\|}{C}}-(CH_2)_n-CH_3$$

wherein $n$ is an integer from 4 to 10,
are prepared by acylating a compound of the general formula (II), $$\text{(II)}$$

wherein R and $\widehat{xy}$ each have the same meanings as defined above, and $R_2$ stands for a group of the formula (VI), (VII) or (VIII), $$-\underset{O}{\overset{\|}{C}}-NH-CH_2-CH-CH_2-O-CH_2-CH=CH_2 \quad \text{(VI)}$$
$$\phantom{xxxxxxx}OH$$

$$-\underset{O}{\overset{\|}{C}}-NH-CH-(CH_2)_3-NH-\overset{\|}{\underset{NH}{C}}-NH-NO_2 \quad \text{(VII)}$$
$$\phantom{xxxxxx}CH_2-OH$$

$$-CH_2-NH-\underset{O}{\overset{\|}{C}}-CH-NH-\overset{O}{\overset{\|}{C}}-O-CH_2-C_6H_5 \quad \text{(VIII)}$$
$$\phantom{xxxxxxxx}CH_2-OH$$

with a $C_{6-12}$ carboxylic acid or a $C_{6-12}$ carboxylic acid halide.

The new compounds of the general formula (I) and their acid addition salts can be used as antidepressants and antiserotonine agents with prolonged effects.

5 Claims, No Drawings

COMPOUNDS WITH ERGOLINE SKELETON

This invention relates to new compounds with ergoline skeleton and pharmaceutical compositions containing the same.

The new compounds according to the invention correspond to the general formula (I)

$$\text{(I)}$$

wherein
R stands for hydrogen or methyl group,
$\overset{\frown}{xy}$ stands for a group of the formula $$-CH=\overset{|}{C}- \quad \text{or} \quad -CH_2-\overset{|}{CH}-,$$

and
$R_1$ stands for a group of the formula (III), (IV) or (V)

$$-\underset{\underset{O}{\|}}{C}-NH-CH_2-\underset{\underset{\underset{O}{\|}}{O-C-(CH_2)_n-CH_3}}{\overset{|}{CH}}-CH_2-O-CH_2-CH=CH_2 \quad \text{(III)}$$

$$-\underset{\underset{O}{\|}}{C}-NH-\underset{\underset{\underset{O}{\|}}{CH_2-O-C-(CH_2)_n-CH_3}}{\overset{|}{CH}}-(CH_2)_3-NH-\underset{\underset{NH}{\|}}{C}-NH-NO_2 \quad \text{(IV)}$$

$$-CH_2-NH-\underset{\underset{O}{\|}}{C}-\underset{\underset{\underset{O}{\|}}{CH_2-O-C-(CH_2)_n-CH_3}}{\overset{|}{CH}}-NH-\overset{O}{\overset{\|}{C}}-O-CH_2-C_6H_5 \quad \text{(V)}$$

wherein n is an integer of from 4 to 10.

The acid addition salts of the above compounds are also embraced by the scope claimed.

As known, serotonine (5-hydroxy-tryptamine) plays an important pathophysiological role in various diseases, such as in the carcinoid syndrome and in allergic-anaphylaxic reactions connected with inflammation. Furthermore, this compound is regarded to be the causative substance of migraine.

In the British patent specification No. 1,345,546 dihydrolysergic acid derivatives possessing very specific antiserotonine activities were described. Of these compounds 1-methyl-dihydrolysergyl-nitroargininole bimaleate proved to exert a very strong 5-hydroxy-tryptamine receptor-antagonizing effect both under in vivo and in vitro conditions.

Up to the present no composition ensuring a prolonged antiserotonine effect has been proposed for therapeutical use. Such compounds would, however, be of great importance, since the presently used short-acting antiserotonine agents do not provide a stable blood level, and between acute migrainic attacks the majority of the patients neglects to take the drug regularly.

It is also known that drugs suitable for the treatment of the different forms of depression are of very great importance in the treatment of patients with psychic disorders. Of the known compounds primarily the tricyclic antidepressants proved to be applicable for the treatment of the severe forms of depression. It is a great problem, however, that up to now there was known no antidepressant agent possessing prolonged effects, providing a stable blood level as a consequence of the retarded biotransformation and thus being applicable for the treatment of chronic diseases.

The above considerations hold also for neuroleptics with prolonged effects.

The invention aims at providing novel compounds with ergoline skeleton which can be used in the therapy as antiserotonine, antidepressive or neuroleptic agents with prolonged activities.

The invention is based on the recognition that the $C_{6-12}$ carboxylic acid esters of the compounds having the general formula (II), $$\text{(II)}$$

primarily the respective capric esters can be used to great advantage in the treatment of various vascular or psychic disorders as substances with prolonged effects.

Thus the invention relates to new compounds of the general formula (I) as well as the acid addition salts thereof, wherein R, $\overset{\frown}{xy}$, $R_1$ and n each have the same meanings as defined above. Of these compounds lysergic acid-(3'-allyloxy2'-decanoyloxy-propyl)-amide $$(R = H, \overset{\frown}{xy} = -CH=\overset{|}{C}-, R_1 = /III/, n = 8),$$

$R_1 = /III/$, $n = 8$), 1-methyl-dihydrolysergyl-nitroargininole decanoate $$(R = CH_3, \overset{\frown}{xy} = -CH_2-\overset{|}{CH}-, R_1 = /IV/, n = 8)$$

and 1,6-dimethyl-8β-(N-benzyloxycarbonyl-O-decanoyl-L-serylamidomethyl)-ergoline

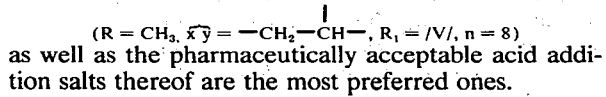

as well as the pharmaceutically acceptable acid addition salts thereof are the most preferred ones.

As a process for the preparation of the new compounds having the general formula (I), wherein R, $\overline{xy}$, $R_1$ and $n$ each have the same meanings as defined above, and the acid addition salts thereof, a compound of the general formula (II), wherein R and $\overline{xy}$ each have the same meanings as defined above, and $R_2$ stands for a group of the formula (VI), (VII) or (VIII),

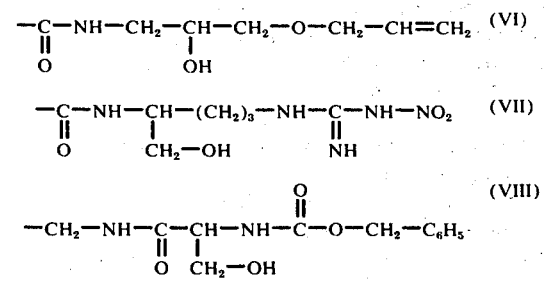

is acylated with a $C_{6-12}$ carboxylic acid or a $C_{6-12}$ carboxylic acid halide, and, if desired, the thus-obtained ester is converted into its acid addition salt formed with an organic or mineral acid.

According to a preferred method a $C_{6-12}$ acyl halide is used as acylating agent, and the acylation is performed in an organic solvent, in the presence of a base. As base, e.g., a nitrogen-containing organic base, such as dicyclohexylamine, triethylamine, N-methylmorpholine or pyridine, whereas as organic solvent, e.g., a ketone, tetrahydrofuran, dimethyl formamide, dioxane, pyridine or acetonitrile can be utilized. The acylation is performed at a temperature between −30° and +10° C, preferably at a temperature between −20° and 0° C. Of the acyl halides hexanecarbonyl chloride and capryl chloride are the most preferred acylating agents, whereas of the free carboxylic acids hexadecarboxylic acid and capric acid are the most preferred ones.

When using a free carboxylic acid as acylating agent, the acylation is performed preferably in an organic solvent, particularly in pyridine, in the presence of a water scavenger, preferably dicyclohexyl carbodiimide.

According to a preferred method 1-methyl-dihydrolysergyl-nitroargininole is dissolved in pyridine, and a benzene solution of hexanecarbonyl chloride is added dropwise to the pyridine solution. The reaction mixture is poured onto ice water, the mixture is extracted with chloroform, the chloroform extract is evaporated, and the residue is subjected to chromatography. If desired, the thus-obtained free base can be converted into its acid addition salt by treatment with an organic or mineral acid. The salt formation is effected preferably with maleic acid, hydrochloric acid, methanesulfonic acid or tartaric acid in an alcoholic medium. The term "salt" refers primarily to the pharmacologically acceptable non-toxic salts.

According to a further preferred method lysergic acid-(3′-allyloxy-2′-oxy-propyl)-amide is dissolved in acetonitrile, and an acetone solution of capryl chloride and an acetone solution of dicyclohexylamine are added. The separated dicyclohexylammonium salt is filtered off, the filtrate is evaporated, the residue is admixed with water, and the aqueous mixture is extracted with a halogenated hydrocarbon. The extract is evaporated. If desired, the thus-obtained residue can be converted into its acid addition salt by treatment with an organic or mineral acid.

Those starting substances of the general formula (II), wherein R stands for hydrogen or methyl, $\overline{xy}$ stands for

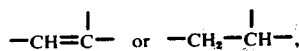

and $R_2$ stands for a group of the formula (VI) or (VII) can be prepared as follows: lysergic acid or a reactive derivative thereof, preferably the corresponding pentachlorophenyl ester is reacted with an amine having the formula (IX) or (X)

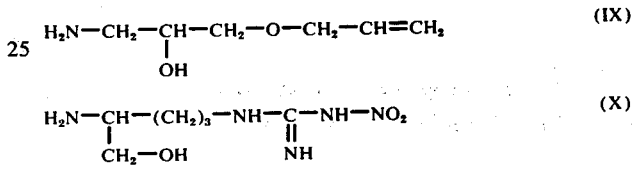

according to the process described in Hungarian patent specification No. 163,546, and the obtained product is optionally subjected to N-methylation and/or hydrogenated in positions 9 and 10.

When a compound of the general formula (II), wherein $R_2$ stands for a group of the formula (VIII) is to be prepared, elimoclavine is reacted with mesyl or tosyl chloride, the obtained sulfonic acid ester is contacted immediately with ammonia, subsequently the double bond located between positions 8 and 9 is hydrogenated, and the thus-obtained substance is reacted with the pentachlorophenyl ester of N-benzyloxycarbonyl-L-serine.

The prolonged antiserotonine effect of 1-methyl-dihydrolysergyl-nitroargininole decanoate bimaleate (Compound A) was examined according to the method of Bonta, I.L. (Arch. Int. Pharmacodyn. 132, 147 /1961/). Groups consisting of 10 rats each were used in the individual tests. An injectable liquid of 0.1 ml. volume, containing 5μug. of serotonine creatinine sulfate, was injected into the plantar region of the animals, and subsequently the animals were treated intramuscularly with 0.5 mg./kg. of the active agent, admixed with sunflower oil. As reference substance 1-methyl-dihydrolysergyl-nitroargininole bimaleate (Compound B), the most preferred one of the compounds disclosed in Hungarian Pat. No. 161,090, was used. The results of the above tests are summarized in Table 1.

Table 1

| Time (hours) | Inhibition of plantar oedema, % | |
|---|---|---|
| | Compound A | Compound B |
| 1 | 58 | 69 |
| 3 | 80 | 60 |
| 5 | 76 | 60 |
| 24 | 70 | 45 |
| 48 | 58 | 25 |
| 72 | 37 | 5 |

Table 1-continued

| Time (hours) | Inhibition of plantar oedema, % | |
|---|---|---|
| | Compound A | Compound B |
| 96 | 3 | 0 |

As it appears from the data of the above Table, a single intramuscular injection of 1-methyl-dihydrolysergyl-nitroargininole-decanoate bimaleate inhibits the plantar oedema of rats provoked by serotonine for a prolonged period. The depot injection with antiserotonine effect can be used for the prevention of migrainic attacks, and renders the treatment of the patients more simple and more safe. Using the above new compound according to the invention, the combinations containing salicylates, amidazophenum and phenacetine, utilized so far to relieve the migrainic headache and known to exert undesirable side effects on the stomach, the haematopoietic organs and the kidneys, can be excluded from the therapy.

No side-effects occur upon the prolonged administration of the compounds according to the invention. By the prolonged administration of the novel compounds, the effects causing cardiopulmonary aorta fibrosis, ureteral fibrosis and retroperitoneal fibrosis can be avoided.

Lysergic acid-(3'-allyloxy-2'-decanoyloxy-propyl)-amide bimaleate, a new compound according to the invention, exerts a prolonged antidepressive effect when administered parenterally. This compound antagonizes the reserpine and tetrabenazine-provoked central nervous depressive phenomena in a manner analogous to the tricyclic antidepressants, but is far more potent than the latter compounds. The above compound also increases the effect of amphetamine. Lysergic acid-(3'-allyloxy-2'-decanoyloxy-propyl)-amide bimaleate differs in character from the tricyclic antidepressants to some extent, since it also exerts a slight psychostimulant effect on mice and rats. These effects appear in the oral or parenteral dosage range of from 1 to 10 mg./kg. The reserpine and tetrabenazine-antagonizing effects of the above compound appear shortly after the administration of the injection, and last for a prolonged period.

Lysergic acid-(3'-allyloxy-2'-decanoyloxy-propyl)-amide bimaleate can be used for the treatment of various psychic depressions in the form of an intramuscular depot injection containing 10 to 200 mg. of the active agent. This compound can be used to great advantage for the treatment of patients who require a prolonged treatment but tolerate the treatment poorly or are inconsistent in taking of the medicine. Depending on the dosage and the rate of biotransformation, a single dosage of the above compound may ensure a prolonged effect lasting for 1 to 4 weeks.

The new compounds according to the invention can be converted into pharmaceutical compositions by admixing them with inert, pharmaceutically acceptable carriers, diluents and/or auxiliary agents. As carrier or diluent primarily vegetable oils, such as olive oil, sesame oil and sunflower oil can be applied. The injectable compositions containing the new compounds of the general formula (I) can be filled into ampoulles of 1 to 2 ml. volume, or vials of 5 to 10 ml. volume.

The thus-formed pharmaceutical compositions are used in the therapy as compositions ensuring prolonged effects. They can be administered preferably in a dosage of 12.5 to 100 mg. (0.5 to 2.0 ml.) per 1 to 4 weeks.

The invention is elucidated in detail by the aid of the following non-limiting Examples.

EXAMPLE 1

Lysergic acid-(3'-allyloxy-2'-decanoyloxy-propyl)-amide bimaleate

Step A: Lysergic acid-(3'-allyloxy-2'-oxy-propyl)-amide 2.81 g. of lysergic acid hydrazide, dissolved in 100 ml. of 0.1 N hydrochloric acid, are added to 10 ml. of a 1 N aqueous sodium nitrite solution, and thereafter 15 ml. of 1 N hydrochloric acid are added dropwise to the stirred mixture at 2° to 5° C. The mixture is stirred for an additional 15 minutes at 0° to 5° C. Thereafter the mixture is neutralized with saturated sodium bicarbonate solution, and extracted in three portions with a total amount of 2 l. of ether. The etheral fractions are combined, dried over anhydrous potassium carbonate, filtered, and a solution of 1.32 g. of 3-allyloxy-2-oxy-propylamine in 100 ml. of isopropanol is added to the stirred filtrate. The mixture is stirred at room temperature for 4 hours, and thereafter washed with water. The aqueous phase is extracted with 2×50 ml. of chloroform. The organic solutions are combined, dried over anhydrous potassium carbonate, and evaporated to dryness.

Step B: Lysergic acid-(3'-allyloxy-2'-decanoyloxy-propyl)-amide bimaleate 3.82 g. of lysergic acid-(3'-allyloxy-2'-oxy-propyl)-amide (free base) are dissolved in 150 ml. of acetonitrile with stirring, and a solution of 2.1 ml. of capryl chloride in 10 ml. of acetone is added dropwise to the stirred mixture at −10° C. The mixture is stirred and cooled for an additional hour. The separated salt is filtered off, and the filtrate is evaporated. 100 ml. of water and 200 ml. of chloroform are added to the residue, the pH of the aqueous phase is adjusted to 8 with 10% ammonium hydroxide solution, the mixture is shaken, and the organic phase is separated. The aqueous phase is extracted five times more than 100 ml. amounts of chloroform. The organic phases are combined, dried over anhydrous sodium sulfate, and evaporated to dryness. The dry residue is dissolved in ethanol, and converted into its maleate. The thus-obtained lysergic acid-(3'-allyloxy-2'-decanoyloxypropyl)-amide bimaleate melts at 160°–162° C; $(\alpha)_D^{20} = +18.9°$ (C = 0.5, in 50% ethanol). Yield: 5.2 g. (80%).

EXAMPLE 2

1-Methyl-dihydrolysergyl-nitroargininole decanoate 4.72 g. of 1-methyl-dihydrolysergyl-nitroargininole (free base), prepared as described in Example 1 of the British Patent Specification No. 1,345,546 are dissolved in 150 ml. of pyridine with stirring. The solution is cooled to −20° C, and a solution of 15 ml. of capryl chloride in 15 ml. of acetone is added dropwise. The reaction mixture is stirred at −20° C for 30 minutes, then poured into 500 ml. of ice water, and 500 ml. of chloroform are added. The mixture is shaken, the organic phase is separated, and the aqueous phase is extracted with 6×50 ml. of chloroform. The organic phases are combined, dried over anhydrous sodium sulfate, filtered, and the filtrate is evaporated to dryness in vacuo. The residue is subjected to chromatography on a silica gel column (particle size of the filling agent: 0.09 to 0.16 mm.). A 90:4:30 mixture of chloroform, water and ethanol is used as eluting agent. By adding cyclohexan to the mixture 5.7 g. (78%) of 1-methyl-dihydrolysergyl-nitroargininole-decanoate bimaleate are obtained; m.p.: 122°–124° C; $(\alpha)_D^{20}$ = −77.0° (C = 0.5, in pyridine).

EXAMPLE 3

1,6-Dimethyl-8β-(N-benzyloxycarbonyl-O-decanoyl-L-serylamidomethyl)-ergoline hydrochloride Step A: 8β-Aminomethyl-6-methyl-Δ⁸-ergolene 2.55 g. of elimoclavine are suspended in 200 ml. of dry acetonitrile with stirring. The suspension is cooled to 0° C, and a solution of 3.4 ml. of mesyl chloride in 15 ml. of acetonitrile is added slowly and dropwise to the mixture. Subsequently a solution of 5 ml. of dicyclohexylamine in 15 ml. of acetone is added in the same way. The mixture is stirred at room temperature for 3 hours. The separated dicyclohexylammonium salt is filtered off, and 10 ml. of anhydrous liquid ammonia are poured to the stirred filtrate. The mixture is stirred for one hour, then evaporated, and 100 ml. of water and 300 ml. of a 1:4 mixture of isopropanol and chloroform are added to the residue. The pH of the aqueous phase is adjusted to 8 with acetic acid, and the mixture is shaken. The organic phase is separated, and the aqueous phase is extracted with 6×50 ml. of a 1:4 mixture of isopropanol and chloroform. The organic phases are combined, dried over sodium sulfate, filtered, and the filtrate is evaporated to dryness.

Step B: 8β-Aminomethyl-6-methyl-ergoline 2.6 g. of 8β-aminomethyl-6-methyl-Δ⁸-ergolene, prepared as described in Step A above, are dissolved in 500 ml. of dry ethanol, and 10 g. of Raney nickel are added to the solution. The mixture is hydrogenated for 2 hours at a temperature of 65° C and under a pressure of 65 atmospheres. Thereafter the catalyst is filtered off, and the filtrate is evaporated.

Step C: 8β-Aminomethyl-1,6-dimethyl-ergoline

A mixture of 8 ml. of dry ethanol and 10 ml. of dry ether is added dropwise, within 20 minutes to the stirred solution of 1.9 g. of metallic sodium in 300 ml. of liquid ammonia. Upon this procedure the initially deep blue solution turns gradually colorless. Thereafter 2.53 g. of dried 8β-aminomethyl-6-methyl-ergoline, prepared as described in Step B above, are added, the mixture is stirred until complete dissolution occurs (for 5 minutes), and then a solution of 6.6 g. of methyl iodide in 8 ml. of dry ether is added dropwise, within 5 minutes to the mixture at −40° C. The mixture is stirred at the same temperature for an additional 30 minutes, thereafter it is warmed cautiously and ammonia is removed in vacuo. The residue is dissolved in a mixture of 100 ml. of isopropanol and 400 ml. of chloroform, 150 ml. of water are added to the solution, and the pH of the aqueous phase is adjusted to 8 with acetic acid. The mixture is shaken, the organic phase is separated, and the aqueous phase is extracted with 3×100 ml. of a 1:4 mixture of isopropanol and chloroform. The organic phases are combined, dried over sodium sulfate, filtered and evaporated. The residue is subjected to chromatography using a column filled with 40 g. of silica gel in order to remove the impurities optionally present. A 30:2:11 mixture of chloroform, water and methanol is used as eluting agent.

Step D: 1,6-Dimethyl-8β-(N-benzyloxycarbonyl-L-serylamidomethyl)-ergoline 6.0 g. of N-benzyloxycarbonyl-L-serine pentachlorophenyl ester, prepared as described in J. Org. Chem. 32, 3696 (1967), are dissolved in a mixture of 200 ml. of dry acetonitrile and 50 ml. of dimethyl formamide, and a solution of 2.7 g. of 8β-aminomethyl-1,6-dimethyl-ergoline, prepared as described in Step C above, in 25 ml. of dimethyl formamide is added. The mixture is stirred for 2 hours and then evaporated. The residue is purified by chromatography (adsorbent: a column filled with 60 g. of silica gel; eluting agent: a 30:0.5:7.5 mixture of chloroform, water and ethanol).

Step E: 1,6-Dimethyl-8β-(N-benzyloxycarbonyl-O-decanoyl-L-serylamidomethyl)-ergoline hydrochloride 4.8 g. of 1,6-dimethyl-8β-(N-benzyloxycarbonyl-L-serylamidomethyl)-ergoline, prepared as described in Step D above, are dissolved in 48 ml. of pyridine. The solution is cooled to 0° C, and 2.7 g. of dicyclohexyl carbodiimide and 3.4 g. of capric acid are added. The reaction mixture is allowed to stand at room temperature for 16 hours. The separated crystalline dicyclohexyl urea is filtered off, and the filtrate is evaporated. The residue is dissolved in 200 ml. of water, and 500 ml. of chloroform are added to the solution. The mixture is shaken, the organic phase is separated, and extracted with 6×50 ml. of chloroform. The organic phases are combined, dried over anhydrous sodium sulfate, filtered, and the filtrate is evaporated to dryness in vacuo.

The residue is passed through a column filled with silica gel (particle size: 0.08 to 0.16 mm.). A 90:4:36 mixture of chloroform, water and ethanol is used as eluting agent. The effluent containing the purified product is treated with alcoholic hydrochloric acid. The separation of the salt is enhanced by adding ether to the mixture 4.9 g. of 1,6-dimethyl-8β-(N-benzyloxycarbonyl-O-decanoyl-L-serylamidomethyl)-ergoline hydrochloride are obtained; m.p.: 120°–121° C, $(\alpha)_D^{20}$ = −29° (c = 0.5, in 50% aqueous ethanol).

EXAMPLE 4

1-Methyl-dihydrolysergyl-nitroargininole-enanthate bimaleate

This compound is prepared as described in Step B of Example 1, using 4.72 g. of 1-methyl-dihydrolysergyl-nitroargininole, 1.7 ml. of enanthyl chloride and 2.0 ml. of dicyclohexylamine. The purified product is treated with an isopropanol solution of maleic acid. In this way 5.25 g. (75%) of 1-methyl-dihydrolysergyl-nitroargininole-enanthate bimaleate are obtained; m.p.: 115°–117° C, $(\alpha)_D^{20}$ = 42° (c = 0.5, in 50% ethanol).

EXAMPLE 5

2'-Enanthyl-oxymethyl-(N-benzyloxycarbonyl-seryl-1-methyl-dihydrolysergamide hydrochloride This compound is prepared as described in Step B of Example 1, using 3.6 g. of N-benzyloxycarbonyl-1-methyl-dihydrolysergamide, 1.7 ml. of enanthyl chloride and 2.0 ml. of dicyclohexylamine. The purified product is treated with alcoholic hydrochloric acid. In this way 4.1 g. (74%) of 2'-enanthyl-oxymethyl-N-benzyloxycarbonyl-seryl-1-methyl-dihydrolysergamide hydrochloride are obtained; m.p.: 121°–123° C; $(\alpha)_D^{20}$ = −31° (c = 0.5, in 50% ethanol).

EXAMPLE 6

Lysergic acid-(3'-allyloxy-2'-enanthyloxy-propyl)amide bimaleate

This compound is prepared as described in Example 2, using 3.82 g. of lysergic acid-(3'-allyloxy-2'-oxy-propyl)amide and/10 ml. of enanthyl chloride. The purified product is treated with an alcoholic solution of maleic acid. In this way 5.5 g. (85%) of lysergic acid-(3'-allyloxy-2'-enanthyloxy-propyl)-amide bimaleate are obtained; m.p.: 165°–167° C; $(\alpha)_D^{20} = +20°$ (c = 0.5, in 50% ethanol).

EXAMPLE 7

Intramuscular injection

Composition per ampoulle:

| | |
|---|---|
| 1-methyl-dihydrolysergyl-nitroargininole-decanoate | 10 mg. |
| sesame oil | 1.0 ml. |
| benzylalcohol | 1.5 ml. |

What we claim is:

1. A compound of the formula wherein
R is hydrogen or methyl,
$\overset{\frown}{xy}$ is $$-CH{=}\overset{|}{C}- \text{ or } -CH_2-\overset{|}{CH}-,$$

and $R_1$ is $$-\underset{O}{\overset{\|}{C}}-NH-\underset{CH_2-O-\underset{O}{\overset{\|}{C}}-(CH_2)_n-CH_3}{\overset{|}{CH}}-(CH_2)_3-NH-\underset{NH}{\overset{\|}{C}}-NH-NO_2$$

wherein n is an integer of from 4 to 10, or a pharmaceutically acceptable acid addition salt thereof.

2. 1-Methyl-dihydrolysergyl-nitroargininole decanoate or a pharmaceutically acceptable acid addition salt thereof.

3. A compound as claimed in claim 1, in which n is equal to 8.

4. A pharmaceutical composition having a prolonged antiserotonine effect containing as active ingredient a compound as in claim 1 in the amount of 10 to 200 mg per unit dosage, together with a pharmaceutically acceptable carrier, diluent and/or auxiliary agent.

5. A process for the preparation of a pharmaceutical composition, in which a compound as claimed in claim 1 is converted into a pharmaceutical composition by admixing it with a pharmaceutically acceptable carrier, diluent and/or auxiliary agent.

* * * * *